(12) United States Patent  
Shiue et al.

(10) Patent No.: US 11,074,468 B2  
(45) Date of Patent: Jul. 27, 2021

(54) METHOD OF LIVENESS DETECTION AND RELATED DEVICE

(71) Applicant: FaceHeart Inc., Hsinchu (TW)

(72) Inventors: Tsuey-Huey Shiue, Hsinchu (TW); Bing-Jhang Wu, Chiayi (TW); Kuan-Hung Chen, Hsinchu (TW); Wen-Chung Chen, Taoyuan (TW)

(73) Assignee: FaceHeart Inc., Hsinchu (TW)

( * ) Notice: Subject to any disclaimer, the term of this patent is extended or adjusted under 35 U.S.C. 154(b) by 0 days.

(21) Appl. No.: 16/732,331

(22) Filed: Jan. 1, 2020

(65) Prior Publication Data

US 2021/0064898 A1 Mar. 4, 2021

(30) Foreign Application Priority Data

Aug. 29, 2019 (TW) .................................. 108130941

(51) Int. Cl.  
*G06K 9/00* (2006.01)

(52) U.S. Cl.  
CPC ..... *G06K 9/00906* (2013.01); *G06K 9/00255* (2013.01); *G06K 2009/00939* (2013.01)

(58) Field of Classification Search  
CPC ........... G06K 9/00906; G06K 9/00255; G06K 2009/00939; G06K 9/0012; G06K 2009/00932; G06K 9/0002; G06K 9/00026; G06K 9/00288; G06K 9/00885; G06K 9/00892; G06K 9/036; G06K 9/6215; G06K 9/00201; G06K 9/6288; G06K 9/629; G06K 9/00335; G06K 9/00355; G06K 9/00114; G06K 9/00228; G06K 9/00234; G06K 9/3233; G06K 9/00107; G06K 9/00765; G06K 9/00771; G06K 9/00899; G06K 9/00046; G06K 9/0004; G06K 2209/01; G06K 9/00087; G06K 9/2036; G06K 9/209; G06K 9/22; G06K 9/46; G06K 9/00302; G06K 9/00268; G06K 9/00362; G06F 16/9535; G06F 16/248; G06F 16/29; G06F 16/24578; G06F 16/337; G06F 16/48; G06F 21/32; G06F 8/30; G06F 3/017; G06F 1/3206; G06F 21/629; G06F 21/88; G06F 16/95; G06F 21/31; G06F 21/445; G06F 21/552; G06F 21/577; G06F 21/6218;

(Continued)

(56) References Cited

U.S. PATENT DOCUMENTS

2004/0240712 A1* 12/2004 Rowe ................. A61B 5/14546  
382/124  
2007/0268485 A1* 11/2007 Polonskiy ............ G06K 9/2018  
356/300

(Continued)

FOREIGN PATENT DOCUMENTS

| CN | 108366759 A | 8/2018 |
|---|---|---|
| CN | 110110591 A | 8/2019 |
| TW | I652040 B | 3/2019 |

*Primary Examiner* — Nimesh Patel  
(74) *Attorney, Agent, or Firm* — Winston Hsu

(57) ABSTRACT

A method of liveness detection for a computing device comprises acquiring at least one full cycle of a remote photoplethysmography, rPPG, signal from a skin image, extracting at least one rPPG waveform characteristic from the full cycle of the rPPG signal, and determining whether the skin image includes a life according to the extracted rPPG waveform characteristic.

9 Claims, 4 Drawing Sheets

(58) Field of Classification Search
CPC ..... G06F 2221/2101; G06F 2221/2115; G06F 2221/2119; G06T 2207/30076; G06T 7/0012; G06T 2207/10016; G06T 7/75; G06T 2207/20216; G06T 2207/30008; G06T 7/0016; G06T 2207/30201; G06T 7/73; G06T 2207/20021; G06T 2207/20056; G06T 7/0014; G06T 7/11; G06T 7/20; G06T 7/254; G06T 7/90; G06T 7/187; G06T 2207/10064; G06T 2207/20212; G06T 7/136; G06T 2207/10088; G06N 20/00; G06N 7/005; G06N 3/006; G06N 5/02; G06N 7/00; G06N 3/004; G06N 5/048; G01J 2005/0077; G01J 2005/0085; G01J 5/12; G01J 5/0025; G01S 7/415; G01S 13/66; G01S 13/867; G01S 7/41; G01S 13/56; G01S 13/86; G01S 13/888; G01S 13/931; G01S 19/42; G01S 13/02; G01S 13/89; G01S 15/06; G01S 15/10; G01S 15/89; G01S 19/17; G01S 5/02; G01S 2013/462; G01S 7/40; G01S 7/411; H04L 63/1483; H04L 63/1491; G02F 1/13338; G02F 1/133504; G02F 1/133606; G02F 1/133607; G02F 1/1335; G02B 6/00; G02B 6/0051; G02B 6/0055; G02B 6/0076

See application file for complete search history.

(56) References Cited

U.S. PATENT DOCUMENTS

| | | | |
|---|---|---|---|
| 2010/0113952 A1* | 5/2010 | Raguin | G06K 9/036 600/509 |
| 2016/0371555 A1* | 12/2016 | Derakhshani | G06K 9/00228 |
| 2018/0239955 A1* | 8/2018 | Rodriguez | G06F 21/32 |
| 2019/0313915 A1* | 10/2019 | Tzvieli | A61B 5/165 |
| 2020/0156648 A1* | 5/2020 | Zhang | G06K 9/00255 |

* cited by examiner

METHOD OF LIVENESS DETECTION AND RELATED DEVICE

BACKGROUND OF THE INVENTION

1. Field of the Invention

The present invention relates to a method of liveness detection, and more particularly, to a method and device for identifying an image as a living image or a fake image with remote photoplethysmography, rPPG.

2. Description of the Prior Art

Conventional liveness detection is realized by color textures, image reflection coefficients, and image depth information of the image, to prevent people from deceiving the face recognition system by a printed paper, photo, video, or 3D mask. However, this mechanism cannot effectively distinguish from high-quality or high-resolution images for avoiding deception. In addition, there are some mechanisms that require the user to be identified to make an active response such as blinking or mouth opening, which results in a poor user experience.

There is also a mechanism for realizing liveness detection with physiological signals, which is mainly based on remote photoplethysmography, rPPG. In detail, rPPG is a non-contact detection method for detecting human heartbeat waveform and heart rate by using a camera, so as to determine whether a face in the captured image is a living face. Note that, the heart activity of the human body is used for producing a physiological signal, namely a change in the amount of subcutaneous microvessel congestion, which affects an absorption rate of light by the blood, and thus can be used for detecting changes in brightness of skin caused by the blood flow. The concept of rPPG is to detect physiological signals (hereafter called rPPG signal) by analyzing the color variations in the skin image. In a word, the rPPG signal can be used for indicating a variety of physiological information, such as cardiac cycle changes, intravascular blood volume changes, heartbeat values, and so on. However, the challenges of this technology include light source change and motion interference.

For example, the current method for determining whether the skin image includes a life or living object is required of transforming the rPPG signal to the rPPG spectrum with time-frequency conversion. However, a fake image under a fixed frequency sway or a fixed frequency light source change may generate a cycle signal, so the physiological signal calculated according to the cycle signal, such as the heartbeat value, is easily controlled within the normal heartbeat range, which causes misjudgment of liveness in the skin image. In addition, the time-frequency transform requires a large number of rPPG signals for calculation, so the rPPG spectrum will be stable after collecting a considerable number of signals, which cause that the subsequent face recognition system cannot be operated in time.

Moreover, the rPPG spectrum obtained by the time-frequency transform is subjected to spectral disorder calculation to determine whether a life or living object exists. However, in the case of a fixed frequency sway or a fixed frequency light source change, a cycle signal is generated, such that the spectrum turbulence is also within the acceptable range, resulting in misjudgment of liveness. Besides, an approach with cross-correlation performed on multiple rPPG signals obtained in different interest areas for wave similarity calculations between these areas still has the above problems.

SUMMARY OF THE INVENTION

It is therefore an objective to provide a method of liveness detection and a related device, for improving the misjudgment of living organisms caused by light source changes and motion interference, to solve the above problem.

The present invention discloses a method of liveness detection for a computing device. The method comprises acquiring at least one full cycle of a remote photoplethysmography, rPPG, signal from a skin image, extracting at least one rPPG waveform characteristic from the full cycle of the rPPG signal, and determining whether the skin image includes a life according to the extracted rPPG waveform characteristic.

The present invention further discloses a computing device for liveness detection. The computing device comprises a processing unit, for executing a program code, and a storage unit, coupled to the processing unit, for storing the program code, wherein the program code instructs the processing unit to perform the following steps: acquiring at least one full cycle of a remote photoplethysmography, rPPG, signal from a skin image, extracting at least one rPPG waveform characteristic from the full cycle of the rPPG signal, and determining whether the skin image includes a life according to the extracted rPPG waveform characteristic.

The present invention further discloses a liveness detection device. The liveness detection device comprises a signal acquiring unit, for acquiring at least one full cycle of a remote photoplethysmography, rPPG, signal from a skin image, a waveform characteristic extracting unit, for extracting at least one rPPG waveform characteristic from the full cycle of the rPPG signal, and a determining unit, for determining whether the skin image includes a life according to the extracted rPPG waveform characteristic.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
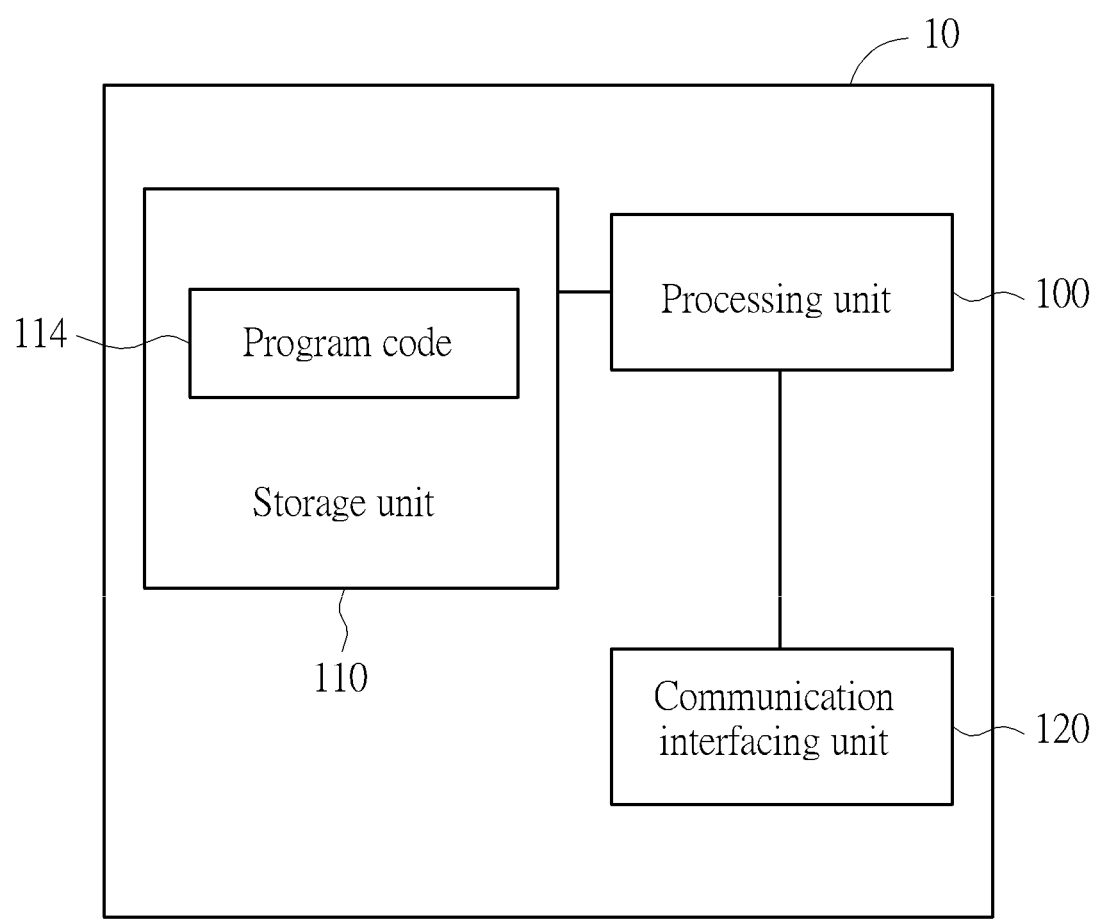
FIG. 1 is a schematic diagram of a liveness detection device according to the present disclosure.

FIG. 1 is a schematic diagram of the liveness detection device 10. The liveness detection device 10 may be a local computing device or a cloud device, and includes a processing unit 100 such as a microprocessor or Application Specific Integrated Circuit (ASIC), a storage unit 110 and a communication interfacing unit 120. The storage unit 110 may be any data storage device that can store program code 114, for access by the processing unit 100 to execute. Examples of the storage unit 110 include but are not limited to a subscriber identity module (SIM), read-only memory (ROM), flash memory, random-access memory (RAM), CD-ROMs, magnetic tape, hard disk, and optical data storage device. The communication interfacing unit 120 is applied with a wire or wireless communication for exchange signals with other devices (e.g. a camera and/or a display device). For example, the communication interface unit 120 receives an image from the camera and transmits it to the processing unit 100, and the processing unit 100 transmits the executed result to the display device. Therefore, the display device can indicate the detecting result of the liveness detection device 10, such as the presence of a real living object (e.g. a living face) in the image, or a fake image that does not have a real living object, so as to notify the security system or generate a warning.

Figure 2:
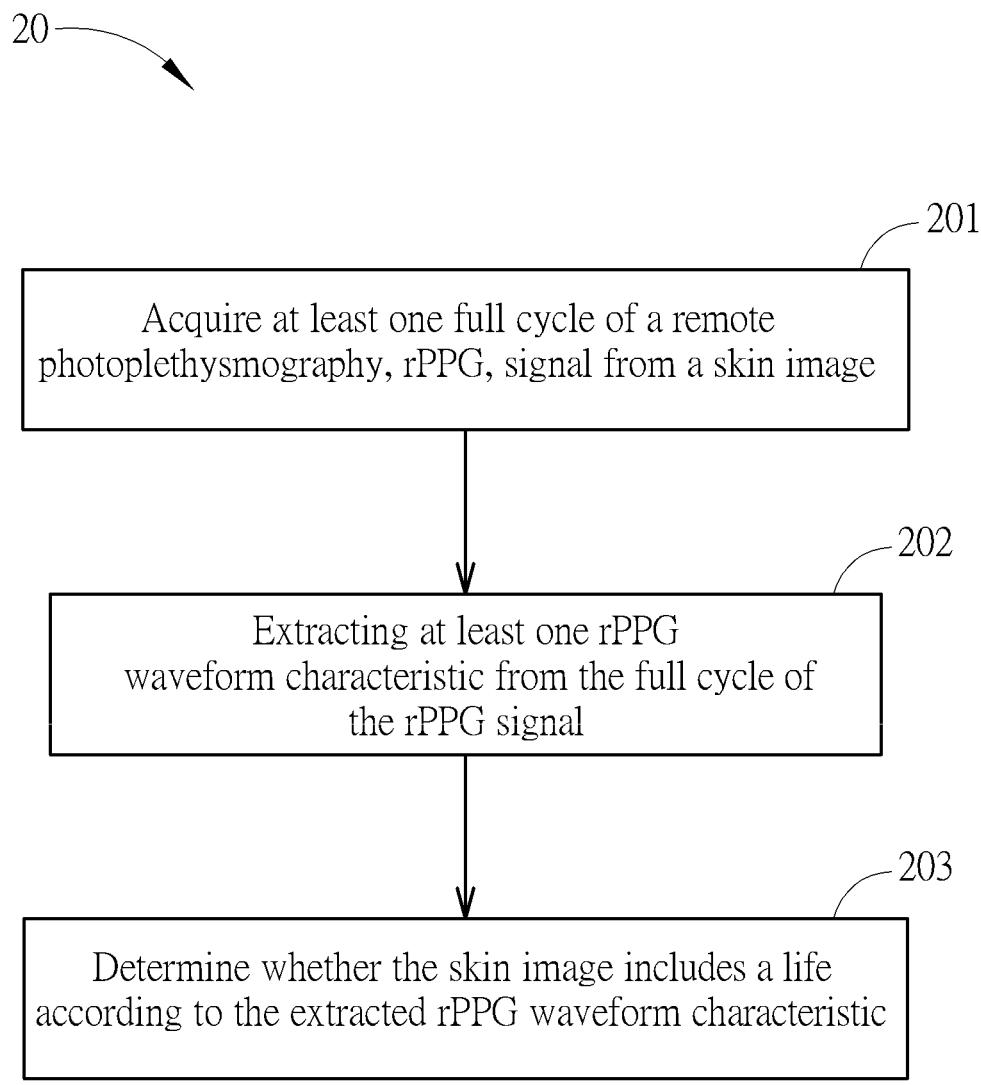
FIG. 2 is a flowchart of liveness detection process according to the present disclosure.

Please refer to FIG. 2, which is a flowchart of the liveness detection process 20 according to an embodiment of the present disclosure. The operation of the liveness detection device 10 of FIG. 1 could be summarized as the liveness detection process 20, which is compiled into the program code 114 and includes the following steps:

Step 201: Acquire at least one full cycle of a remote photoplethysmography, rPPG, signal from a skin image.

Step 202: Extract at least one rPPG waveform characteristic from the full cycle of the rPPG signal.

Step 203: Determine whether the skin image includes a life according to the extracted rPPG waveform characteristic.

Figure 3:
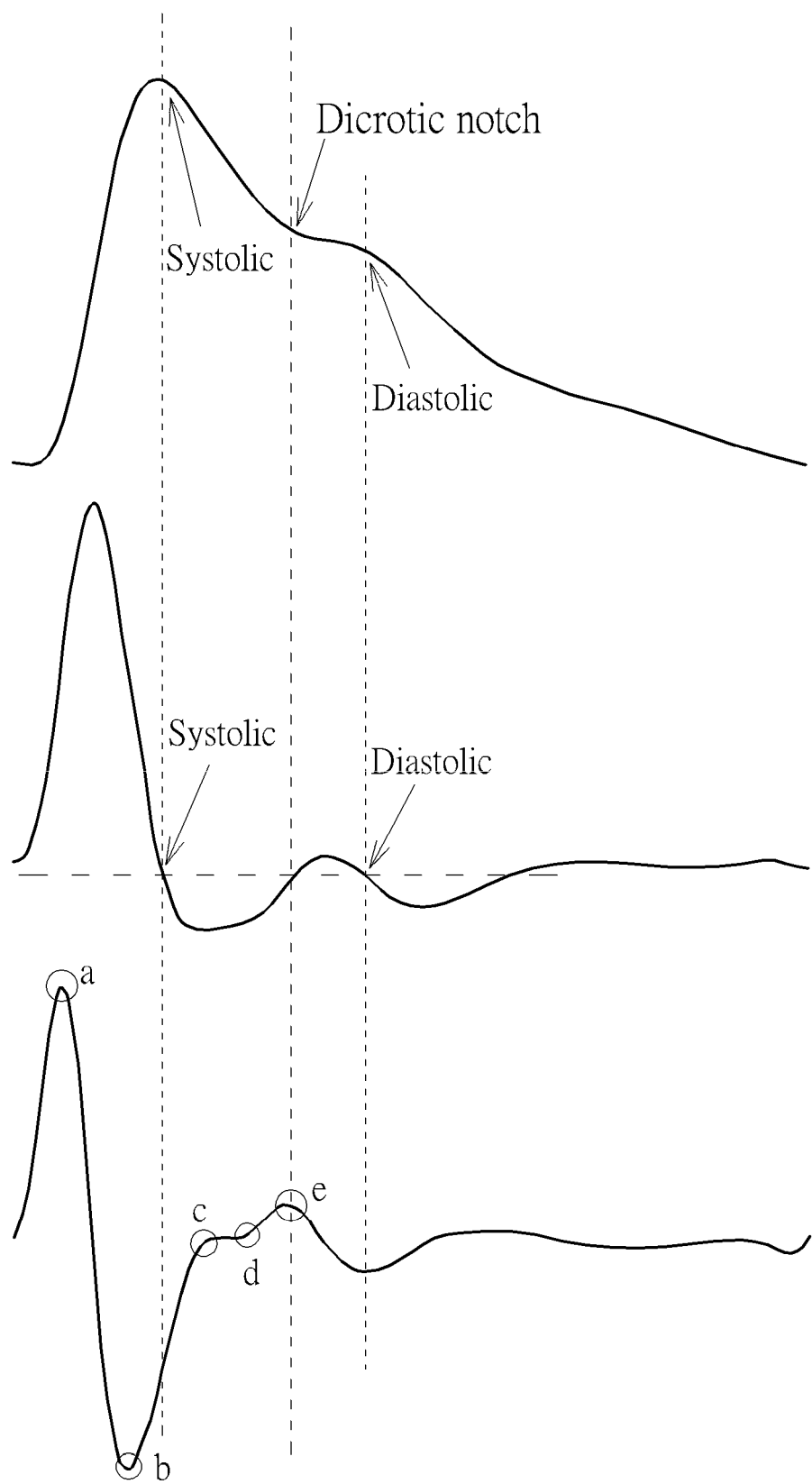
FIG. 3 is a schematic diagram of a waveform characteristic according to the present disclosure.

According to the liveness detection process 20, the full cycle of the rPPG signal is used for obtaining the rPPG waveform characteristic, so as to determine whether a living object is in the captured skin image. Reference is made to FIG. 3, which is a schematic diagram of a waveform characteristic according to the present disclosure. In detail, the rPPG waveform characteristic includes dicrotic notch wave, systolic wave, diastolic wave, systolic-diastolic wave, a first order differential feature of the rPPG signal as shown in the middle of FIG. 3, and a second order differential feature of the rPPG signal as shown in the bottom of FIG. 3. In addition, as shown in FIG. 3, the second order differential feature of the rPPG signal includes at least one of an early systolic positive wave "a", an early systolic negative wave "b", a late systolic reincreasing wave "c", a late systolic redecreasing wave "d", and an early diastolic positive wave "e". In other words, when the rPPG waveform characteristic includes any of dicrotic notch wave, systolic wave, diastolic wave, systolic-diastolic wave, a first order differential feature of the rPPG signal, and a second order differential feature of the rPPG signal, the liveness detection device 10 determines that there is a living object in the skin image. Otherwise, the liveness detection device 10 determines that the skin image is a fake image if the rPPG waveform characteristic does not include any of the abovementioned waves.

In an embodiment, the liveness detection device 10 could perform wave related operations or algorithms, such as signal amplification or noise filtering, to enhance the rPPG waveform characteristic.

Figure 4:
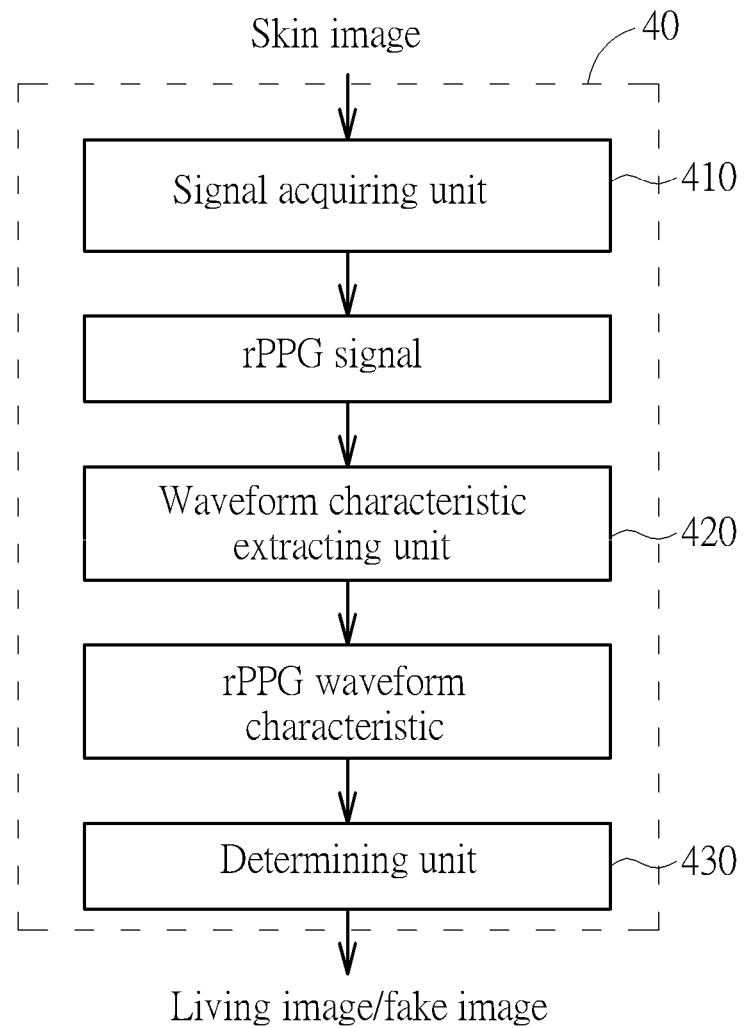
FIG. 4 is a schematic diagram of an operation of a liveness detection device according to the present disclosure.

Reference is made to FIG. 4, which is a schematic diagram of an operation of the liveness detection device 40 according to the present disclosure. The liveness detection device 40 includes the signal acquiring unit 410, the waveform characteristic extracting unit 420 and the determining unit 430. The signal acquiring unit 410 is used for acquiring at least one full cycle of a rPPG signal from a skin image and transmitting the rPPG signal to the waveform characteristic extracting unit 420. The waveform characteristic extracting unit 420 is used for extracting at least one rPPG waveform characteristic from the full cycle of the rPPG signal and transmitting the extracted rPPG waveform characteristic to the determining unit 430. The determining unit 430 is used for determining whether the skin image includes a life or a living object according to the extracted rPPG waveform characteristic and a predetermined threshold. In an embodiment, the determining unit 430 may determine the probability of occurrence of the waveform characteristic and/or adjust the threshold according to the mathematical template obtained by the database statistics or the machine learning technique, thereby determining whether the rPPG waveform characteristic exists. For example, if a parameter corresponding to the rPPG waveform characteristic is higher than the threshold, the determining unit 430 determines that the skin image contains a living object; otherwise, if it is lower than the threshold, the determining unit 430 determines that the skin image does not include a living object.

The abovementioned steps of the processes including suggested steps can be realized by means that could be a hardware, a firmware known as a combination of a hardware device and computer instructions and data that reside as read-only software on the hardware device or an electronic system. Examples of hardware can include analog, digital and mixed circuits known as microcircuit, microchip, or silicon chip. Examples of the electronic system can include a system on chip (SOC), system in package (SiP), a computer on module (COM) and the liveness detection device 10 and 40.

In summary, the present invention provides a method and related device for liveness detection, which utilizes the rPPG cycle signal to obtain its waveform characteristic to directly determine whether a living object exists in the image without time-frequency transform operation. With such manner, misjudgment of liveness caused by the fixed frequency sway or fixed frequency light source change is avoided and higher performance of liveness detection is provided.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of liveness detection for a computing device, the method comprising:
acquiring at least one full cycle of a remote photoplethysmography, rPPG, signal from a skin image;
extracting at least one rPPG waveform characteristic from the full cycle of the rPPG signal; and
determining whether the skin image includes a life according to the extracted rPPG waveform characteristic;
wherein the extracted rPPG waveform characteristic comprises a first order differential feature of the rPPG signal and a second order differential feature of the rPPG signal.

2. The method of claim 1, wherein the step of determining whether the skin image includes the life according to the extracted rPPG waveform characteristic comprises:
determining that the skin image includes the life when the extracted rPPG waveform characteristic includes at least one of a dicrotic notch wave, a systolic wave, a diastolic wave, a systolic-diastolic wave.

3. The method of claim 1, wherein the second order differential feature of the rPPG signal includes at least one of an early systolic positive wave, an early systolic negative wave, a late systolic reincreasing wave, a late systolic redecreasing wave, and an early diastolic positive wave.

4. A computing device for liveness detection, the computing device comprising:
   a processing unit, for executing a program code; and
   a storage unit, coupled to the processing unit, for storing the program code, wherein the program code instructs the processing unit to perform the following steps:
      acquiring at least one full cycle of a remote photoplethysmography, rPPG, signal from a skin image;
      extracting at least one rPPG waveform characteristic from the full cycle of the rPPG signal; and
      determining whether the skin image includes a life according to the extracted rPPG waveform characteristic;
      wherein the extracted rPPG waveform characteristic comprises a first order differential feature of the rPPG signal and a second order differential feature of the rPPG signal.

5. The method of claim 4, wherein the program code further instructs the processing unit to perform the following steps:
   determining that the skin image includes the life when the extracted rPPG waveform characteristic includes at least one of a dicrotic notch wave, a systolic wave, a diastolic wave, a systolic-diastolic wave.

6. The method of claim 4, wherein the second order differential feature of the rPPG signal includes at least one of an early systolic positive wave, an early systolic negative wave, a late systolic reincreasing wave, a late systolic redecreasing wave, and an early diastolic positive wave.

7. A liveness detection device comprising:
   a signal acquiring circuit, configured to acquire at least one full cycle of a remote photoplethysmography, rPPG, signal from a skin image;
   a waveform characteristic extracting circuit, configured to extract at least one rPPG waveform characteristic from the full cycle of the rPPG signal; and
   a determining circuit, configured to determine whether the skin image includes a life according to the extracted rPPG waveform characteristic;
      wherein the extracted rPPG waveform characteristic comprises a first order differential feature of the rPPG signal and a second order differential feature of the rPPG signal.

8. The liveness detection device of claim 7, wherein the determining circuit is further used for determining that the skin image includes the life when the extracted rPPG waveform characteristic includes at least one of a dicrotic notch wave, a systolic wave, a diastolic wave, a systolic-diastolic wave.

9. The liveness detection device of claim 7, wherein the second order differential feature of the rPPG signal includes at least one of an early systolic positive wave, an early systolic negative wave, a late systolic reincreasing wave, a late systolic redecreasing wave, and an early diastolic positive wave.

* * * * *